United States Patent [19]

Shinohara et al.

[11] Patent Number: 5,136,072
[45] Date of Patent: Aug. 4, 1992

[54] THEXYL $C_1$–$C_4$ ALKYL DIALKOXY SILANE

[75] Inventors: Toshio Shinohara, Yawata; Motoaki Iwabuchi, Annaka, both of Japan

[73] Assignee: Shin-Etsu Chemical Co., Ltd., Tokyo, Japan

[21] Appl. No.: 798,515

[22] Filed: Nov. 26, 1991

[30] Foreign Application Priority Data

Nov. 30, 1990 [JP] Japan ................................ 2-334568
Apr. 17, 1991 [JP] Japan ................................ 3-112415

[51] Int. Cl.$^5$ ............................................. C07F 7/18
[52] U.S. Cl. ...................................................... 556/482
[58] Field of Search ....................................... 556/482

[56] References Cited

U.S. PATENT DOCUMENTS

| | | | |
|---|---|---|---|
| 2,985,678 | 5/1961 | Chappelow et al. | 556/482 X |
| 3,291,742 | 12/1966 | Millward | 556/482 X |
| 3,576,030 | 4/1971 | Alsgaard | 556/482 X |
| 3,839,383 | 10/1974 | Kotzsch et al. | 556/482 X |
| 4,695,643 | 9/1987 | Oertle et al. | 556/482 X |

*Primary Examiner*—Paul F. Shaver
*Attorney, Agent, or Firm*—Henry T. Burke

[57] ABSTRACT

Thexyl ($C_1$–$C_4$) alkyl dialkoxy silanes are proposed as a class of novel organosilicon compounds such as thexyl methyl dimethoxy silane and thexyl n-butyl dimethoxy silane. These silane compounds can be synthesized by several different routes. For example, thexyl methyl dimethoxy silane is prepared starting from methyl phenyl chlorosilane which is subjected to the hydrosilation reaction with 2,3-dimethyl-2-butene to introduce a thexyl group and the compound is converted by the reaction with hydrogen chloride into thexyl methyl dichlorosilane which is methoxylated by the reaction with methyl alcohol.

4 Claims, 2 Drawing Sheets

THEXYL $C_1$-$C_4$ ALKYL DIALKOXY SILANE

BACKGROUND OF THE INVENTION

The present invention relates to a novel organosilicon compound. More particularly, the invention relates to a dialkoxy silane compound having a thexyl, i.e. 1,1 2-trimethylpropyl, group and an alkyl group of 1 to 4 carbon atoms bonded to the silicon atom.

SUMMARY OF THE INVENTION

The novel organosilicon compound is a thexyl ($C_1$-$C_4$)-alkyl dialkoxy silane expressed by the general formula

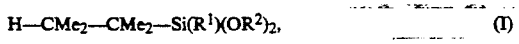

$$H\text{—}CMe_2\text{—}CMe_2\text{—}Si(R^1)(OR^2)_2, \quad (I)$$

in which Me is a methyl group, $R^1$ is an alkyl group having 1 to 4 carbon atoms and $R^2$ is an alkyl group.

Although the above defined silane compound of the invention can be prepared by several different synthetic routes, preferable methods depend on the alkyl group denoted by $R^1$ in the above given general formula (1). When $R^1$ is a methyl group, for example, thexyl methyl phenyl chlorosilane prepared from methyl phenyl chlorosilane is reacted with hydrogen chloride gas to be converted into thexyl methyl dichlorosilane which can readily be alkoxylated by the dehydrochlornation reaction with an alcohol. When $R^1$ is a n-butyl group and $R^2$ is a methyl group, the compound can be synthesized by the reaction of thexyl trimethoxy silane and n-butyl lithium or by the reaction of a thexyl trichlorosilane with n-butyl lithium to form a thexyl n-butyl dichlorosilane which is then methoxylated by the dehydrochlorination reaction with methyl alcohol.

DETAILED DESCRIPTION OF THE PREFERRED EMBODIMENTS

Figure 1:
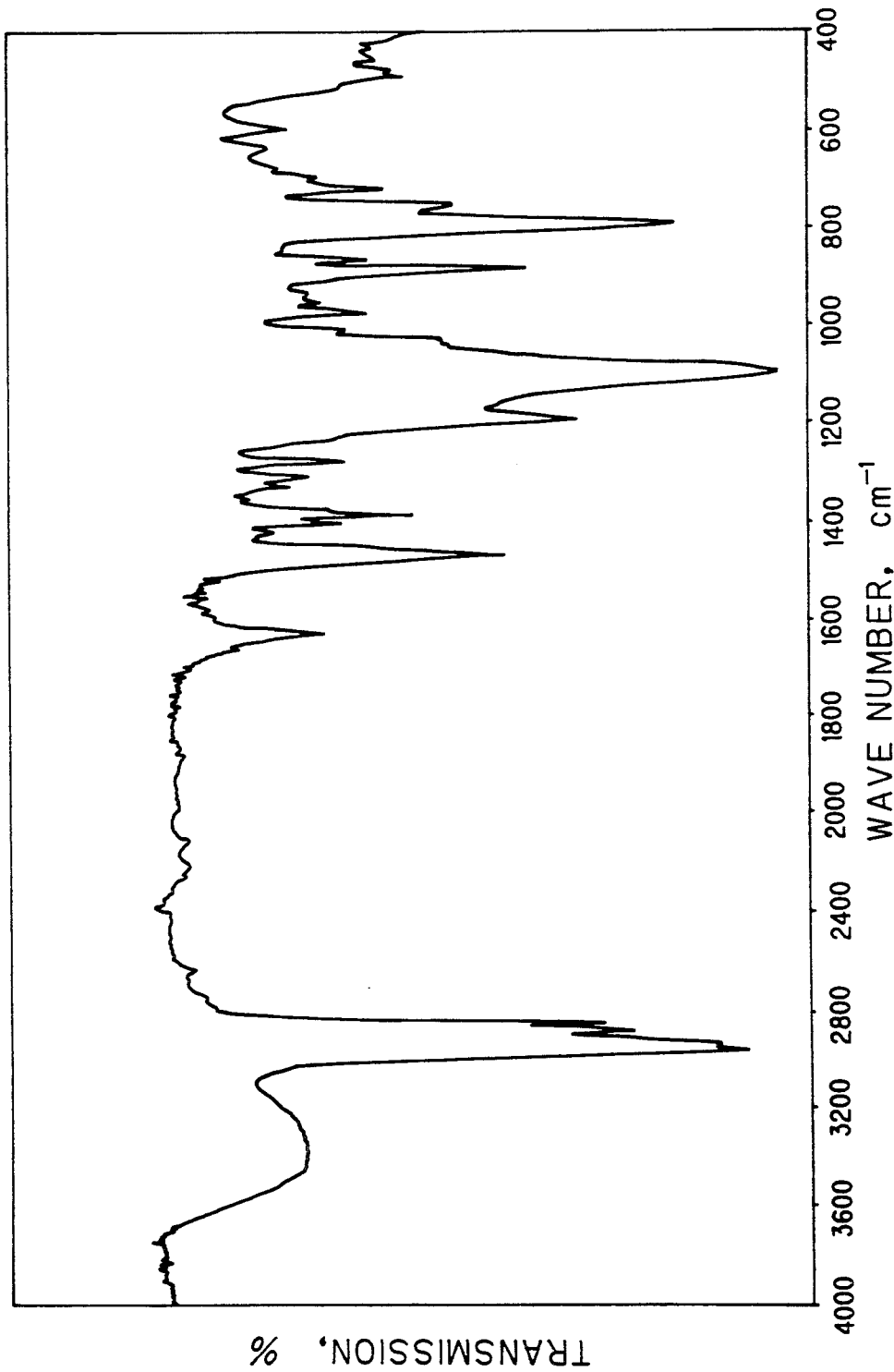
FIG. 1 shows an infrared absorption spectrum of the thexyl methyl dimethoxy silane prepared in Example 1.

It is known in the prior art that an organosilane or polysiloxane compounds having alkoxy groups and linear-chain hydrocarbon groups bonded to the silicon atoms are used to impart water-repellency to the surface of various kinds of substrate materials. In such an application, the water-repellency obtained by the treatment is generally increased when the chain length of the hydrocarbon group is increased. Further, such an organosilane or polysiloxane compound can be used as an additive to the catalyst for the olefin polymerization while the effect as a catalyst additive is enhanced when the chain length of the long-chain hydrocarbon group is increased. These advantages, however, are accompanied by a disadvantage due to the difficulty and inconvenience in the preparation and use of the compounds as a consequence of the increase in the boiling point and/or melting point of the compound. In addition, the rate of increase in the advantages is decreased as the chain length of the hydrocarbon group is increased not to compensate for the disadvantages caused thereby. Accordingly, the inventors have undertaken extensive investigations to obtain an alkoxy-containing organosilane compound capable of fully exhibiting the advantages with minimized disadvantages above mentioned leading to the establishment of the present invention.

Thus, the novel compound of the invention is a thexyl ($C_1$-$C_4$)alkyl dialkoxy silane which is represented by the above given general formula (1), in which $R^1$ is an alkyl group having 1 to 4 carbon atoms such as methyl, ethyl, n-propyl, isopropyl, n-butyl and tert-butyl groups and $R^2$ is an alkyl group having, preferably, 1 to 4 carbon atoms or, more preferably, is a methyl group. Examples of the inventive thexyl ($C_1$-$C_4$)alkyl dialkoxy silane accordingly include thexyl methyl dimethoxy silane, thexyl ethyl dimethoxy silane, thexyl n-propyl dimethoxy silane, thexyl isopropyl dimethoxy silane, thexyl n-butyl dimethoxy silane, thexyl tert-butyl dimethoxy silane and the like as well as those compounds corresponding to the above named ones by replacing the methoxy group with another alkoxy group such as ethoxy group, propoxy group, butoxy group and the like.

By virtue of the hydrolyzability of the two alkoxy groups and the bulkiness of the thexyl group, the above proposed novel organosilane compound, i.e. thexyl alkyl dialkoxy silane, is a promising useful material as a surface-treatment agent of various kinds of building materials including wooden materials and masonry and concrete materials. Further, the compound readily forms a coordination compound with metallic magnesium and compounds of titanium or aluminum so that it is useful as an additive in a complex catalyst for the polymerization of olefins such as propylene to give a highly isotactic polypropylene.

As is described above, the thexyl ($C_1$-$C_4$)alkyl dialkoxy silane of the invention can be synthesized in several different ways of synthetic route, of which the most preferable method depends on the alkyl group denoted by $R^1$ in the general formula (I).

Thexyl methyl dimethoxy silane as one of the inventive silane compounds, for example, can be prepared by the following three-step synthetic route including the so-called hydrosilation reaction. In the first step of the synthetic route, methyl phenyl chlorosilane or a solution thereof in a hydrocarbon solvent of a suitable concentration in the range, for example, from 1 to 5 moles/liter is admixed with anhydrousaluminum chloride $AlCl_3$ in an amount of 0.001 to 50% by moles based on the amount of the silane compound to form a mixture, into which 2,3-dimethyl-2-butene in an amount of 1.0 to 1.1 moles per mole of the silane compound is added dropwise at a temperature of $-20°$ to $+40°$ C. or, preferably, $+10°$ to $+30°$ C. over a period of 0.1 to 5 hours followed by an aging period of 1 to 5 hours at room temperature to complete the reaction of hydrosilation. The reaction mixture is then freed from aluminum chloride by filtration and the filtrate is concentrated by evaporating the solvent, if used, and the unreacted reactants. Distillation of the thus concentrated reaction product under reduced pressure gives a fraction boiling at about 103° C. under a pressure of 3 mmHg which is thexyl methyl phenyl chlorosilane.

In the second step following the above described hydrosilation reaction of the first step, the thexyl methyl phenyl chlorosilane obtained above is dissolved in a suitable hydrocarbon solvent, preferably, in a concentration of 1 to 5 moles/liter and dry hydrogen chloride gas is blown into this solution kept at a temperature of $-20°$ to $+40°$C. at a rate of 0.001 to 0.1 mole/minute per mole of the thexyl methyl phenyl chlorosilane over a period of 0.5 to 5 hours. After completion of the reaction, the reaction mixture is freed from residual aluminum chloride by filtration and the filtrate is concentrated by evaporating the solvent and hydrogen chloride. Distillation of the thus concentrated reaction product under reduced pressure gives a fraction boiling at about 75° C. under a pressure of 30 mmHg which is thexyl methyl dichlorosilane.

The third step of the synthetic route is the methoxylation of the above obtained thexyl methyl dichlorosilane by the dehydrochlorination reaction with methyl alcohol. Thus, 1 mole of the thexyl methyl dichlorosilane is admixed dropwise with a n-hexane solution of methyl alcohol and urea or DBU, i.e. 1,5-diazabicyclo[5.4.0]undec-5-ene, as an acid acceptor, of which the concentration of methyl alcohol is from 5 to 20% by weight, the amount of methyl alcohol is from 2.0 to 2.5 moles per mole of the thexyl methyl dichlorosilane and the amount of the acid acceptor is approximately equimolar to methyl alcohol, at a temperature of 10° to 45° C. or, preferably, 20° to 30° C. over a period of 0.1 to 3 hours followed by an aging period of 1 to 5 hours at 20° to 65° C. to complete the reaction. The reaction mixture after completion of the reaction separates into layers upon standing so that the liquid in the lower layer containing the hydrochloride of the acid acceptor is discarded and the hexane solution in the upper layer is taken and neutralized by adding propylene oxide thereinto followed by removal of the solvent by evaporation under normal pressure and distillation of the concentrate under reduced pressure to give the desired thexyl methyl dimethoxy silane as a fraction boiling at about 82° C. under a pressure of 30 mmHg.

Thexyl n-butyl dimethoxy silane or the compound of the invention of which the group denoted by $R^1$ in the general formula (1) is a n-butyl group can be synthesized in two different synthetic routes described below.

In one of the routes, thexyl trimethoxy silane, which can be prepared by the dehydrochlorination reaction between thexyl trichlorosilane as a known compound and methyl alcohol, is reacted with n-butyl lithium to substitute a n-butyl group for one of the methoxy groups. Alternatively, the starting material is thexyl trihalogenosilane, e.g., thexyl trichlorosilane, which is reacted with a limited amount of n-butyl lithium to produce thexyl n-butyl dihalogenosilane which is then subjected to the dehydrohalogenation reaction with methyl alcohol in the presence of an acid acceptor.

In the above described synthetic methods for the preparation of thexyl n-butyl dimethoxy silane, the silane compound as the starting material can be diluted, if necessary, with an organic solvent such as ether solvents, e.g., tetrahydrofuran, diethyl ether and dibutyl ether, and hydrocarbon solvents, e.g., n-pentane and n-hexane, in a concentration of at least 0.01 mole/liter. n-Butyl lithium is used preferably as a solution in an organic solvent such as ether and hydrocarbon solvents including the above named ones in a concentration of 0.01 to 4 moles/liter. The reaction of the starting silane compound and n-butyl lithium can be performed at a temperature of $-78°$ C. to $+20°$ C. by adding n-butyl lithium or a solution thereof to the silane compound or a solution thereof or vice versa. Removal of the precipitates of lithium salt such as lithium methoxide from the reaction mixture by filtration and the solvent by evaporation is followed by distillation of the thus concentrated reaction mixture to give the thexyl n-butyl dimethoxy silane as a fraction boiling at about 86° C. under a pressure of 3 mmHg or thexyl n-butyl dihalogenosilane, which latter compound can be readily methoxylated by the reaction with methyl alcohol in an amount of at least twice of the equimolar amount.

The thexyl alkyl dialkoxy silane or, in particular, thexyl alkyl dimethoxy silane obtained in the above described method is a colorless liquid. By virtue of the controlled hydrolyzability of the methoxy groups and bulkiness of thexyl group therein, the silane compound is useful as a surface-treatment agent of various building materials including wooden, concrete and marble materials to impart the surface with water-repellency Further, the silane compound readily forms a coordination compound with metallic magnesium and compounds of aluminum or titanium so that the silane compound can be a promising substitute for diphenyl dimethoxy silane conventionally used as an additive in complex catalysts for the olefin polymerization to give advantages that the step of the de-ashing substantially can be omitted due to the outstandingly high activity of the catalyst and an isotactic polymer can be selectively obtained even by omitting the purification process.

In the following, examples are given to illustrate the synthetic procedure and characterization of the inventive silane compounds in more detail. Further, an application example is given to illustrate the usefulness of the inventive compounds as an additive in the complex catalyst for the olefin polymerization.

EXAMPLE 1

Into a reaction mixture prepared by adding 12.7 g (0.095 mole) of aluminum chloride to 149 g (0.952 mole) of methyl phenyl chlorosilane at 20° C. under agitation were added dropwise 85.3 g (1.015 moles) of 2,3-dimethyl-2-butene over a period of 90 minutes and the reaction mixture was further agitated at 20° C. for additional 5 hours followed by stripping of the unreacted reactants under reduced pressure. The thus concentrated reaction mixture was diluted by admixing 200 ml of benzene to give a solution into which dry hydrogen chloride gas was blown at 20° C. at a rate of 0.005 mole/minute for 3 hours. Thereafter, the reaction mixture was freed from volatile matters by stripping under a reduced pressure of 100 mmHg at 20° C.

The residual liquid after stripping of the volatile matter as above was added dropwise into a mixture of 22.4 g (0.70 mole) of methyl alcohol, 42 g (0.70 mole) of urea and 200 ml of n-hexane at 20° C. over a period of 1 hour and the reaction mixture was further agitated for additional 3 hours at 20° C. to complete the reaction.

The reaction mixture after completion of the reaction was freed from the hydrochloride of urea and the thus obtained hexane solution was neutralized by admixing 10 g of propylene oxide followed by the removal of hexane by distillation under normal pressure. Distillation of the residue under reduced pressure gave 60.3 g of a clear, colorless liquid as a fraction boiling at 82° C. under a pressure of 30 mmHg. The result of the gas chromatographic analysis indicated that this product consisted substantially of a single component. This product could be identified to be thexyl methyl dimethoxy silane from the results of $^1$H-NMR spectroscopic analysis shown below and the infrared absorption spectrum shown in FIG. 1 of the accompanying drawing so that the above mentioned yield of the product corresponds to 33% of the theoretical value.

$^1$H-NMR ($\delta$, ppm. CDCl$_3$) 3.55 (s, 6H, —OCH$_3$) 1.9 —1.1 (m, 1H, —CH) 1.1 —0.8 (m, 12H, —CH$_3$) 0.13 (s, 3H, —SiCH$_3$)

EXAMPLE 2

Into a mixture of 100 ml of tetrahydrofuran and 103.5 g (0.47 mole) of thexyl trichlorosilane were added dropwise 210 ml of a tetrahydrofuran solution of n-butyl lithium in a concentration of 1.6 moles/liter over a period of 4 hours at a temperature of −78° C. followed by removal of the dry ice bath so that the temperature of the reaction mixture was increased to 10° C. after 1 hour of standing. Thereafter, the temperature of the reaction mixture was gradually increased up to 25° C. When the gas chromatographic analysis indicated completion of the reaction by the disappearance of thexyl trichlorosilane, the salt precipitated in the reaction mixture as a by-product was removed by filtration and the filtrate after concentration by evaporating the solvent was distilled under reduced pressure to give 32 g of a clear, colorless liquid product as a fraction boiling at 103° C. under a pressure of 5 mmHg.

A 10 g portion of the thus obtained liquid was added dropwise into a mixture of 13 g (0.086 mole) of 1,5-diazabicyclo[5.4.0]undec-5-ene (DBU), 3.0 g (0.094 mole) of methyl alcohol and 50 ml of n-hexane at 25° C. and the mixture was agitated for 2 hours to effect the reaction. When the gas chromatographic analysis indicated completion of the reaction by the disappearance of the starting material, the hydrochloride of DBU was removed by filtration and the filtrate after concentration by evaporating the solvent was distilled under reduced pressure to give 7.5 g of a clear, colorless liquid as a fraction boiling at 86° C. under a pressure of 3 mmHg and having a refractive index of 1.4398 at 25° C. This liquid product was found to consist of a single component according to the result of gas chromatography.

Figure 2:
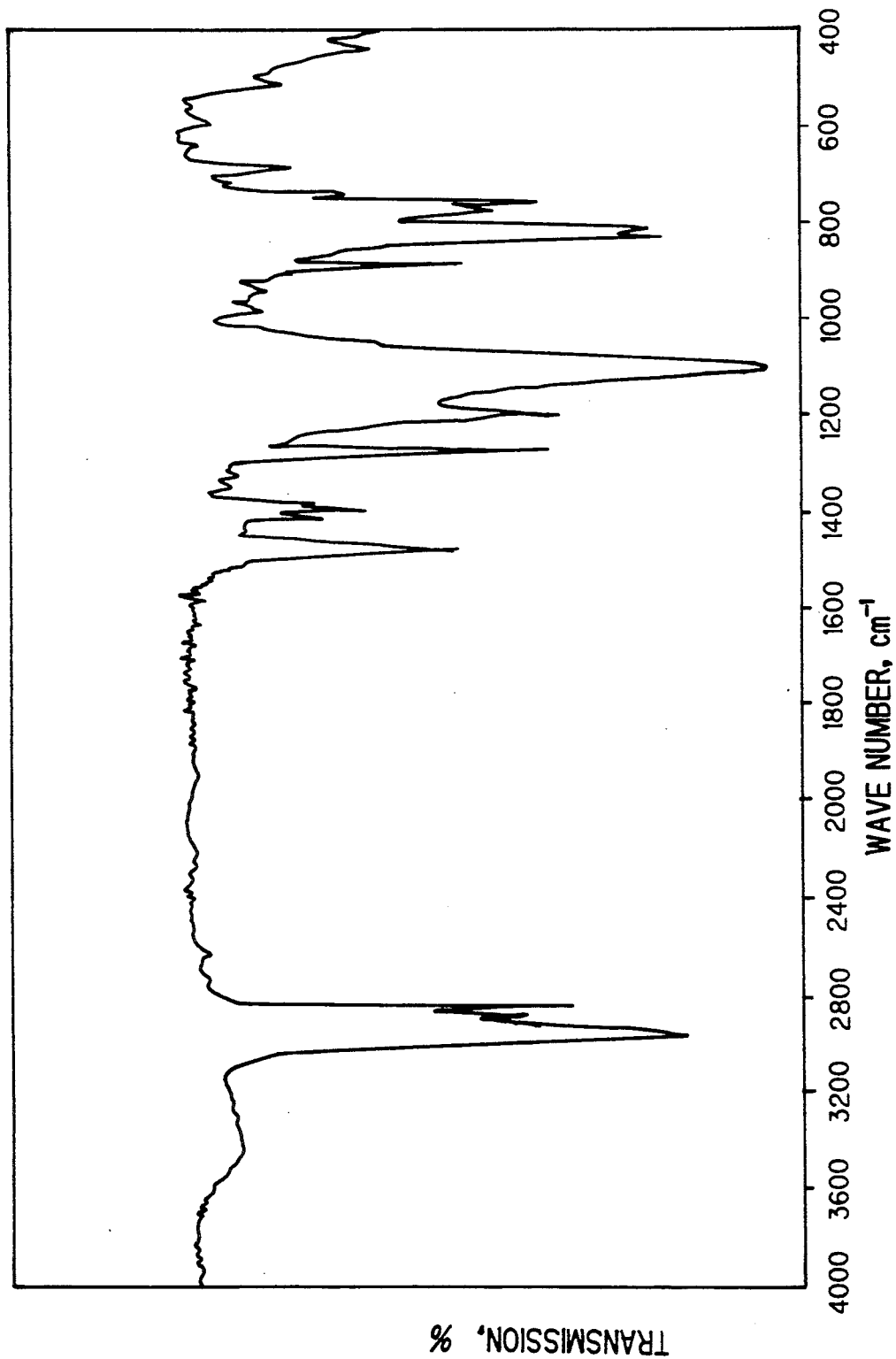
FIG. 2 shows an infrared absorption spectrum of the thexyl n-butyl dimethoxy silane prepared in Example 2.

This liquid product could be identified to be thexyl n-butyl dimethoxy silane from the results of the gas chromatographic-mass spectrometric (GC-MS) analysis and $^1$H-NMR analysis shown below. The above mentioned yield of the product accordingly corresponds to 31% of the theoretical value based on the amount of n-butyl lithium used as the starting material. FIG. 2 shows an infrared absorption spectrum of this product.

GC-MS analysis: M/Z=232 (molecular ion peak)

$^1$H-NMR analysis (δ, ppm, CDC13): 3.57 (m, 6H, -OCH$_3$), 2.2 —1.1 (m, 5H, —CH$_3$—, —CH), 1.1 —0.5 (m, 17H, —CH$_3$, Si-CH$_2$)

EXAMPLE 3

Into 10 ml of a tetrahydrofuran solution containing 2.0 g (0.010 mole) of thexyl trimethoxy silane were added dropwise 6 ml of a tetrahydrofuran solution of n-butyl lithium in a concentration of 1.6 moles/liter at a temperature of −78° C. over a period of 3 hours followed by removal of the dry ice bath so as to increase the temperature of the mixture up to 25° C. to effect the reaction to completion. When the gas chromatographic analysis of the reaction mixture indicated completion of the reaction by the disappearance of the starting silane compound, the precipitated salt was removed by filtration and the filtrate after concentration by the evaporation of the solvent was distilled under reduced pressure to give 1.4 g of a clear, colorless liquid as the product which could be identified to be thexyl n-butyl dimethoxy silane from the results of analysis identical with those obtained in Example 2. Accordingly, this product could be identified to be thexyl n-butyl dimethoxy silane and the above mentioned yield corresponds to 63% of the theoretical value.

APPLICATION EXAMPLE

Into 400 ml of dried n-heptane in a four-necked flask of 1 liter capacity were added, under an atmosphere of nitrogen gas, 76.2 g (0.8 mole) of magnesium chloride and 271.9 g (0.8 mole) of titanium tetrabutoxide to form a reaction mixture which was agitated for 2 hours at 95° C. After cooling to room temperature by standing for a while, the solid matter in the reaction mixture was collected by filtration and washed with dried n heptane. This solid material was again introduced into a four-necked flask of 1 liter capacity and dispersed in 167 ml of n-heptane under an atmosphere of nitrogen gas. This dispersion kept at 25° C. was admixed with a mixture of 83 ml of a n-heptane and 226.7 g (1.3 moles) of tetrachlorosilane by dropwise addition over a period of 1 hour followed by heating at 55°to 57° C. for 3 hours to effect the reaction. Thereafter, a solution prepared by dissolving 10.8 g (0.05 mole) of phthaloyl chloride in 83 ml of n-heptane was added dropwise into the reaction mixture in the flask over a period of 30 minutes followed by a period of 1 hour to complete the reaction at the same temperature. After cooling to room temperature by standing for a while, the solid matter in the reaction mixture was collected by filtration and washed with dried n-heptane. This solid matter was again introduced into a four-necked flask of 1 liter capacity and 136 g (0.8 mole) of tetrachlorosilane were added thereto to effect the reaction at 55°to 57° C. for 1 hour. After cooling to room temperature by standing for a while, the solid matter in the reaction mixture was collected by filtration and washed with dried n-heptane. A 10 g portion of this solid matter was taken in a four-necked flask of 500 ml capacity together with 100 ml of n-heptane under an atmosphere of nitrogen gas and admixed with 1.9 g (0.01 mole) of thexyl methyl dimethoxy silane prepared in Example 1 at 25° C. followed by agitation of the mixture at the same temperature for 2 hours. The solid matter was collected by filtration and washed with dried n-heptane to serve as a catalytic ingredient in the experiment of propylene polymerization described below.

Into a stainless steel autoclave of 1 liter capacity were introduced 500 ml of dried n-heptane and 0.25 g (0.0022 mole) of triethyl aluminum and a dispersion of the same in n-heptane was prepared by agitation at 70° C. for 30 minutes followed by introduction of 200 ml of propylene as liquid thereinto. Thereafter, 6 mg of the catalytic ingredient prepared above were introduced as dispersed in dry n-heptane into the autoclave to effect the polymerization reaction for 3 hours. The yield of polypropylene obtained by repeating the above experiment ranged from 13,000 to 14,000 g per g of the catalyst. This polypropylene resin contained 0.5 to 1.5% by weight of the fraction insoluble in xylene at 25° C. indicating a very low content of atactic polypropylene molecules.

What is claimed is:

1. A thexyl (C$_1$–C$_4$) alkyl dialkoxy silane expressed by the general formula

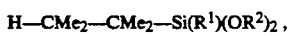

$$H-CMe_2-CMe_2-Si(R^1)(OR^2)_2,$$

in which Me is a methyl group, R$^1$ is an alkyl group having 1 to 4 carbon atoms and R$^2$ is an alkyl group.

2. The thexyl (C$_1$–C$_4$) alkyl dialkoxy silane as claimed in claim 1 in which R$^2$ is a methyl group.

3. Thexyl methyl dimethoxy silane.

4. Thexyl n-butyl dimethoxy silane.

* * * * *